(12) United States Patent
Wybo et al.

(10) Patent No.: US 10,869,616 B2
(45) Date of Patent: Dec. 22, 2020

(54) NEURAL EVENT DETECTION

(71) Applicant: Depuy Synthes Products, Inc., Raynham, MA (US)

(72) Inventors: Christopher Wybo, Highland, MI (US); Aashish Shah, Ann Arbor, MI (US); Tarik Yardibi, Reading, MA (US); Emir Osmanagic, Norwell, MA (US); Darren Scarfe, LaSalle (CA)

(73) Assignee: Depuy Synthes Products, Inc., Raynham, MA (US)

( * ) Notice: Subject to any disclaimer, the term of this patent is extended or adjusted under 35 U.S.C. 154(b) by 330 days.

(21) Appl. No.: 15/995,879

(22) Filed: Jun. 1, 2018

(65) Prior Publication Data

US 2019/0365288 A1 Dec. 5, 2019

(51) Int. Cl.
*A61B 5/11* (2006.01)
*A61B 5/00* (2006.01)
*A61N 1/36* (2006.01)

(52) U.S. Cl.
CPC .......... *A61B 5/1104* (2013.01); *A61B 5/1107* (2013.01); *A61B 5/4893* (2013.01); *A61B 5/7203* (2013.01); *A61B 5/7267* (2013.01); *A61B 5/7282* (2013.01); *A61N 1/36003* (2013.01); *A61B 2505/05* (2013.01); *A61B 2562/0219* (2013.01); *A61B 2562/0261* (2013.01)

(58) Field of Classification Search
CPC ... A61B 5/7267; A61B 5/1104; A61B 5/7203; A61B 2562/0261; A61B 5/1107; A61B 5/7282; A61B 2505/05; A61B 5/4893; A61B 2562/0219; A61N 1/36135; A61N 1/36003

See application file for complete search history.

(56) References Cited

U.S. PATENT DOCUMENTS

| | | |
|---|---|---|
| 3,200,814 A | 8/1965 | Taylor et al. |
| 3,565,080 A | 2/1971 | Ide et al. |
| 3,797,010 A | 3/1974 | Adler et al. |

(Continued)

FOREIGN PATENT DOCUMENTS

| | | |
|---|---|---|
| EP | 1095670 A1 | 5/2001 |
| EP | 1575010 A1 | 9/2005 |

(Continued)

OTHER PUBLICATIONS

International Search Report issued in International Application No. PCT/IB2017/056372 dated Feb. 14, 2018.

(Continued)

*Primary Examiner* — Christine H Matthews
*Assistant Examiner* — Joshua Daryl D Lannu
(74) *Attorney, Agent, or Firm* — Quinn IP Law

(57) ABSTRACT

A neural monitoring system for detecting an artificially-induced mechanical muscle response to a stimulus provided within an intracorporeal treatment area includes a mechanical sensor, a stimulator, and a processor. The processor is configured to provide a periodic stimulus via the stimulator, and monitor the output from the mechanical sensor in an expected response window that follows one stimulus, yet concludes before the application of the next, subsequent stimulus to determine if the stimulus induced a response of the muscle.

20 Claims, 6 Drawing Sheets

(56) References Cited

U.S. PATENT DOCUMENTS

| | | |
|---|---|---|
| 4,155,353 A | 5/1979 | Rea et al. |
| 4,493,327 A | 1/1985 | Bergelson et al. |
| 4,807,642 A | 2/1989 | Brown |
| 4,817,628 A | 4/1989 | Zealear et al. |
| 4,940,453 A | 7/1990 | Cadwell |
| 4,994,015 A | 2/1991 | Cadwell |
| 5,047,005 A | 9/1991 | Cadwell |
| 5,078,674 A | 1/1992 | Cadwell |
| 5,116,304 A | 5/1992 | Cadwell |
| 5,178,145 A | 1/1993 | Rea |
| 5,284,153 A | 2/1994 | Raymond et al. |
| 5,284,154 A | 2/1994 | Raymond et al. |
| 5,482,038 A | 1/1996 | Ruff |
| 5,566,678 A | 10/1996 | Cadwell |
| 5,593,429 A | 1/1997 | Ruff |
| 5,631,667 A | 5/1997 | Cadwell |
| 5,775,331 A | 7/1998 | Raymond et al. |
| 5,860,939 A | 1/1999 | Wofford et al. |
| 5,888,370 A | 3/1999 | Becker et al. |
| 5,993,630 A | 11/1999 | Becker et al. |
| 5,993,632 A | 11/1999 | Becker et al. |
| 6,030,401 A | 2/2000 | Marino |
| 6,093,205 A | 7/2000 | McLeod et al. |
| 6,181,961 B1 | 1/2001 | Prass |
| 6,183,518 B1 | 2/2001 | Ross et al. |
| 6,206,921 B1 | 3/2001 | Guagliano et al. |
| 6,221,082 B1 | 4/2001 | Marino et al. |
| 6,224,603 B1 | 5/2001 | Marino |
| 6,251,140 B1 | 6/2001 | Marino et al. |
| 6,264,659 B1 | 7/2001 | Ross et al. |
| 6,266,394 B1 | 7/2001 | Marino |
| 6,266,558 B1 | 7/2001 | Gozani et al. |
| 6,280,447 B1 | 8/2001 | Marino et al. |
| 6,287,832 B1 | 9/2001 | Becker et al. |
| 6,290,724 B1 | 9/2001 | Marino |
| 6,324,432 B1 | 11/2001 | Rigaux et al. |
| 6,361,508 B1 | 3/2002 | Johnson et al. |
| 6,368,325 B1 | 4/2002 | McKinley et al. |
| 6,387,070 B1 | 5/2002 | Marino et al. |
| 6,387,130 B1 | 5/2002 | Stone et al. |
| 6,436,143 B1 | 8/2002 | Ross et al. |
| 6,466,817 B1 | 10/2002 | Kaula et al. |
| 6,478,805 B1 | 11/2002 | Marino et al. |
| 6,485,518 B1 | 11/2002 | Cornwall et al. |
| 6,491,626 B1 | 12/2002 | Stone et al. |
| 6,500,128 B2 | 12/2002 | Marino |
| 6,519,319 B1 | 2/2003 | Marino et al. |
| 6,530,930 B1 | 3/2003 | Marino et al. |
| 6,533,797 B1 | 3/2003 | Stone et al. |
| 6,540,747 B1 | 4/2003 | Marino |
| 6,564,078 B1 | 5/2003 | Marino et al. |
| 6,638,281 B2 | 10/2003 | Gorek |
| 6,641,708 B1 | 11/2003 | Becker et al. |
| 6,654,634 B1 | 11/2003 | Prass |
| 6,739,112 B1 | 5/2004 | Marino |
| 6,760,616 B2 | 7/2004 | Hoey et al. |
| 6,764,452 B1 | 7/2004 | Gillespie et al. |
| 6,764,489 B2 | 7/2004 | Ferree |
| 6,802,844 B2 | 10/2004 | Ferree |
| 6,805,668 B1 | 10/2004 | Cadwell |
| 6,807,438 B1 | 10/2004 | Brun Del Re et al. |
| 6,843,790 B2 | 1/2005 | Ferree |
| 6,852,126 B2 | 2/2005 | Ahlgren |
| 6,870,109 B1 | 3/2005 | Villarreal |
| 6,887,248 B2 | 5/2005 | McKinley et al. |
| 6,923,814 B1 | 8/2005 | Hildebrand et al. |
| 6,945,973 B2 | 9/2005 | Bray |
| 6,964,674 B1 | 11/2005 | Matsuura et al. |
| 6,972,199 B2 | 12/2005 | Lebouitz et al. |
| 6,981,990 B2 | 1/2006 | Keller |
| 7,001,432 B2 | 2/2006 | Keller et al. |
| 7,025,769 B1 | 4/2006 | Ferree |
| 7,050,848 B2 | 5/2006 | Hoey et al. |
| 7,072,521 B1 | 7/2006 | Cadwell |
| 7,079,883 B2 | 7/2006 | Marino et al. |
| 7,160,303 B2 | 1/2007 | Keller |
| 7,162,850 B2 | 1/2007 | Marino et al. |
| 7,166,113 B2 | 1/2007 | Arambula et al. |
| 7,175,662 B2 | 2/2007 | Link et al. |
| 7,177,677 B2 | 2/2007 | Kaula et al. |
| 7,207,949 B2 | 4/2007 | Miles et al. |
| 7,214,197 B2 | 5/2007 | Prass |
| 7,214,225 B2 | 5/2007 | Ellis et al. |
| 7,216,001 B2 | 5/2007 | Hacker et al. |
| 7,230,688 B1 | 6/2007 | Villarreal |
| 7,236,832 B2 | 6/2007 | Hemmerling et al. |
| 7,267,691 B2 | 9/2007 | Keller et al. |
| 7,296,500 B1 | 11/2007 | Martinelli |
| 7,320,689 B2 | 1/2008 | Keller |
| 7,338,531 B2 | 3/2008 | Ellis et al. |
| 7,341,590 B2 | 3/2008 | Ferree |
| 7,367,958 B2 | 5/2008 | McBean et al. |
| 7,374,448 B1 | 5/2008 | Jepsen et al. |
| 7,379,767 B2 | 5/2008 | Rea |
| 7,470,236 B1 | 12/2008 | Kelleher et al. |
| 7,485,146 B1 | 2/2009 | Crook et al. |
| 7,522,953 B2 | 4/2009 | Kaula et al. |
| 7,527,629 B2 | 5/2009 | Link et al. |
| 7,527,649 B1 | 5/2009 | Blain |
| 7,553,307 B2 | 6/2009 | Bleich et al. |
| 7,555,343 B2 | 6/2009 | Bleich |
| 7,569,067 B2 | 8/2009 | Keller |
| 7,578,819 B2 | 8/2009 | Bleich et al. |
| 7,582,058 B1 | 9/2009 | Miles et al. |
| 7,583,991 B2 | 9/2009 | Rea |
| 7,611,522 B2 | 11/2009 | Gorek |
| 7,618,423 B1 | 11/2009 | Valentine et al. |
| 7,628,813 B2 | 12/2009 | Link |
| 7,634,315 B2 | 12/2009 | Cholette |
| 7,657,308 B2 | 2/2010 | Miles et al. |
| 7,664,544 B2 | 2/2010 | Miles et al. |
| 7,666,195 B2 | 2/2010 | Kelleher et al. |
| 7,668,588 B2 | 2/2010 | Kovacs |
| 7,691,057 B2 | 4/2010 | Miles et al. |
| 7,693,562 B2 | 4/2010 | Marino et al. |
| 7,708,776 B1 | 5/2010 | Blain et al. |
| 7,713,463 B1 | 5/2010 | Reah et al. |
| 7,722,613 B2 | 5/2010 | Sutterlin et al. |
| 7,722,673 B2 | 5/2010 | Keller |
| 7,738,968 B2 | 6/2010 | Bleich |
| 7,738,969 B2 | 6/2010 | Bleich |
| 7,740,631 B2 | 6/2010 | Bleich et al. |
| 7,766,816 B2 | 8/2010 | Chin et al. |
| 7,776,049 B1 | 8/2010 | Curran et al. |
| 7,776,094 B2 | 8/2010 | McKinley et al. |
| 7,785,248 B2 | 8/2010 | Annest et al. |
| 7,785,253 B1 | 8/2010 | Arambula et al. |
| 7,815,682 B1 | 10/2010 | Peterson et al. |
| 7,819,801 B2 | 10/2010 | Miles et al. |
| 7,828,855 B2 | 11/2010 | Ellis et al. |
| 7,833,251 B1 | 11/2010 | Ahlgren et al. |
| 7,857,813 B2 | 12/2010 | Schmitz et al. |
| 7,862,592 B2 | 1/2011 | Peterson et al. |
| 7,862,614 B2 | 1/2011 | Keller et al. |
| 7,867,277 B1 | 1/2011 | Tohmeh |
| 7,883,527 B2 | 2/2011 | Matsuura et al. |
| 7,887,538 B2 | 2/2011 | Bleich et al. |
| 7,887,568 B2 | 2/2011 | Ahlgren |
| 7,887,595 B1 | 2/2011 | Pimenta |
| 7,892,173 B2 | 2/2011 | Miles et al. |
| 7,901,430 B2 | 3/2011 | Matsuura et al. |
| 7,905,840 B2 | 3/2011 | Pimenta et al. |
| 7,905,886 B1 | 3/2011 | Curran et al. |
| 7,914,350 B1 | 3/2011 | Bozich et al. |
| 7,918,849 B2 | 4/2011 | Bleich et al. |
| 7,918,891 B1 | 4/2011 | Curran et al. |
| 7,920,922 B2 | 4/2011 | Gharib et al. |
| 7,927,337 B2 | 4/2011 | Keller |
| 7,935,051 B2 | 5/2011 | Miles et al. |
| 7,938,830 B2 | 5/2011 | Saadat et al. |
| 7,942,104 B2 | 5/2011 | Butcher et al. |
| 7,942,826 B1 | 5/2011 | Scholl et al. |
| 7,946,236 B2 | 5/2011 | Butcher |
| 7,959,577 B2 | 6/2011 | Schmitz et al. |

(56) References Cited

U.S. PATENT DOCUMENTS

| | | |
|---|---|---|
| 7,962,191 B2 | 6/2011 | Marino et al. |
| 7,963,915 B2 | 6/2011 | Bleich |
| 7,963,927 B2 | 6/2011 | Kelleher et al. |
| 7,981,058 B2 | 7/2011 | Akay |
| 7,981,144 B2 | 7/2011 | Geist et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,012,212 B2 | 9/2011 | Link et al. |
| 8,016,767 B2 | 9/2011 | Miles et al. |
| 8,027,716 B2 | 9/2011 | Gharib et al. |
| 8,048,080 B2 | 11/2011 | Bleich et al. |
| 8,050,769 B2 | 11/2011 | Gharib et al. |
| 8,055,349 B2 | 11/2011 | Gharib et al. |
| 8,062,298 B2 | 11/2011 | Schmitz et al. |
| 8,062,300 B2 | 11/2011 | Schmitz et al. |
| 8,062,369 B2 | 11/2011 | Link |
| 8,062,370 B2 | 11/2011 | Keller et al. |
| 8,063,770 B2 | 11/2011 | Costantino |
| 8,068,912 B2 | 11/2011 | Kaula et al. |
| 8,070,812 B2 | 12/2011 | Keller |
| 8,074,591 B2 | 12/2011 | Butcher et al. |
| 8,075,499 B2 | 12/2011 | Nathan et al. |
| 8,075,601 B2 | 12/2011 | Young |
| 8,083,685 B2 | 12/2011 | Fagin et al. |
| 8,083,796 B1 | 12/2011 | Raiszadeh et al. |
| 8,088,163 B1 | 1/2012 | Kleiner |
| 8,088,164 B2 | 1/2012 | Keller |
| 8,090,436 B2 | 1/2012 | Hoey et al. |
| 8,092,455 B2 | 1/2012 | Neubardt et al. |
| 8,092,456 B2 | 1/2012 | Bleich et al. |
| 8,103,339 B2 | 1/2012 | Rea |
| 8,114,019 B2 | 2/2012 | Miles et al. |
| 8,114,162 B1 | 2/2012 | Bradley |
| 8,123,668 B2 | 2/2012 | Annest et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,147,551 B2 | 4/2012 | Link et al. |
| 8,165,653 B2 | 4/2012 | Marino et al. |
| 8,167,915 B2 | 5/2012 | Ferree et al. |
| 8,172,750 B2 | 5/2012 | Miles et al. |
| 8,206,312 B2 | 6/2012 | Farquhar |
| 8,255,044 B2 | 8/2012 | Miles et al. |
| 8,255,045 B2 | 8/2012 | Gharib et al. |
| 8,303,515 B2 | 11/2012 | Miles et al. |
| 8,337,410 B2 | 12/2012 | Kelleher et al. |
| 8,343,065 B2 | 1/2013 | Bartol et al. |
| 8,343,079 B2 | 1/2013 | Bartol et al. |
| 8,394,129 B2 | 3/2013 | Morgenstern Lopez et al. |
| 8,500,653 B2 | 8/2013 | Farquhar |
| 8,500,738 B2 | 8/2013 | Wolf, II |
| 8,517,954 B2 | 8/2013 | Bartol et al. |
| 8,535,224 B2 | 9/2013 | Cusimano Reaston et al. |
| 8,538,539 B2 | 9/2013 | Gharib et al. |
| 8,556,808 B2 | 10/2013 | Miles et al. |
| 8,562,539 B2 | 10/2013 | Marino |
| 8,562,660 B2 | 10/2013 | Peyman |
| 8,568,317 B1 | 10/2013 | Gharib et al. |
| 8,591,431 B2 | 11/2013 | Calancie et al. |
| 8,641,638 B2 | 2/2014 | Kelleher et al. |
| 8,731,654 B2 | 5/2014 | Johnson et al. |
| 8,784,330 B1 | 7/2014 | Scholl et al. |
| 8,792,977 B2 | 7/2014 | Kakei et al. |
| 8,855,822 B2 | 10/2014 | Bartol et al. |
| 8,864,654 B2 | 10/2014 | Kleiner et al. |
| 8,936,626 B1 | 1/2015 | Tohmeh et al. |
| 8,945,004 B2 | 2/2015 | Miles et al. |
| 8,958,869 B2 | 2/2015 | Kelleher et al. |
| 8,983,593 B2 | 3/2015 | Bartol et al. |
| 8,989,855 B2 | 3/2015 | Murphy et al. |
| 8,989,866 B2 | 3/2015 | Gharib et al. |
| 9,014,776 B2 | 4/2015 | Marino et al. |
| 9,014,797 B2 | 4/2015 | Shiffman et al. |
| 9,037,250 B2 | 5/2015 | Kaula et al. |
| 9,066,701 B1 | 6/2015 | Finley et al. |
| 9,084,551 B2 | 7/2015 | Brunnett et al. |
| 9,131,947 B2 | 9/2015 | Ferree |
| 9,192,415 B1 | 11/2015 | Arnold et al. |
| 9,295,396 B2 | 3/2016 | Gharib et al. |
| 9,295,401 B2 | 3/2016 | Cadwell |
| 9,301,711 B2 | 4/2016 | Bartol et al. |
| 9,392,953 B1 | 7/2016 | Gharib |
| 9,446,259 B2 | 9/2016 | Phillips et al. |
| 2001/0031916 A1 | 10/2001 | Bennett et al. |
| 2002/0038092 A1 | 3/2002 | Stanaland et al. |
| 2002/0165590 A1 | 11/2002 | Crowe et al. |
| 2003/0074037 A1 | 4/2003 | Moore et al. |
| 2004/0077969 A1 | 4/2004 | Onda et al. |
| 2004/0082877 A1 | 4/2004 | Kouou et al. |
| 2004/0186535 A1 | 9/2004 | Knowlton |
| 2004/0243018 A1 | 12/2004 | Organ et al. |
| 2005/0075578 A1 | 4/2005 | Gharib et al. |
| 2005/0085741 A1 | 4/2005 | Hoskonen et al. |
| 2005/0102007 A1 | 5/2005 | Ayal et al. |
| 2005/0240086 A1 | 10/2005 | Akay |
| 2005/0245839 A1 | 11/2005 | Stivoric et al. |
| 2005/0280531 A1 | 12/2005 | Fadem et al. |
| 2005/0283204 A1 | 12/2005 | Buhlmann et al. |
| 2006/0020177 A1 | 1/2006 | Seo et al. |
| 2006/0052726 A1 | 3/2006 | Weisz et al. |
| 2006/0135888 A1 | 6/2006 | Mimnagh-Kelleher et al. |
| 2006/0270949 A1 | 11/2006 | Mathie et al. |
| 2007/0038155 A1 | 2/2007 | Kelly et al. |
| 2007/0049826 A1 | 3/2007 | Willis |
| 2007/0232958 A1 | 10/2007 | Donofrio et al. |
| 2007/0265675 A1 | 11/2007 | Lund et al. |
| 2007/0276270 A1 | 11/2007 | Tran |
| 2007/0296571 A1* | 12/2007 | Kolen ............... G08B 21/0446 340/539.11 |
| 2008/0051643 A1 | 2/2008 | Park et al. |
| 2008/0058656 A1 | 3/2008 | Costello et al. |
| 2008/0167695 A1 | 7/2008 | Tehrani et al. |
| 2008/0234767 A1 | 9/2008 | Salmon et al. |
| 2008/0287761 A1 | 11/2008 | Hayter et al. |
| 2008/0306363 A1 | 12/2008 | Chaiken et al. |
| 2008/0306397 A1 | 12/2008 | Bonmassar et al. |
| 2008/0312560 A1 | 12/2008 | Jamsen et al. |
| 2008/0312709 A1 | 12/2008 | Volpe et al. |
| 2009/0036747 A1 | 2/2009 | Hayter et al. |
| 2009/0062696 A1 | 3/2009 | Nathan et al. |
| 2009/0069709 A1 | 3/2009 | Schmitz et al. |
| 2009/0069722 A1 | 3/2009 | Flaction et al. |
| 2009/0076336 A1 | 3/2009 | Mazar et al. |
| 2009/0171381 A1 | 7/2009 | Schmitz et al. |
| 2009/0192416 A1 | 7/2009 | Ernst et al. |
| 2009/0228068 A1 | 9/2009 | Buhlmann et al. |
| 2009/0247910 A1 | 10/2009 | Klapper |
| 2009/0306741 A1 | 12/2009 | Hogle et al. |
| 2009/0318779 A1 | 12/2009 | Tran |
| 2010/0137748 A1 | 6/2010 | Sone et al. |
| 2010/0152619 A1 | 6/2010 | Kalpaxis et al. |
| 2010/0152622 A1 | 6/2010 | Teulings |
| 2010/0152623 A1 | 6/2010 | Williams |
| 2010/0168559 A1 | 7/2010 | Tegg et al. |
| 2010/0262042 A1 | 10/2010 | Kim |
| 2010/0292617 A1 | 11/2010 | Lei et al. |
| 2011/0004207 A1 | 1/2011 | Wallace et al. |
| 2011/0230782 A1 | 9/2011 | Bartol et al. |
| 2011/0237974 A1 | 9/2011 | Bartol et al. |
| 2011/0270121 A1 | 11/2011 | Johnson et al. |
| 2011/0301665 A1 | 12/2011 | Mercanzini et al. |
| 2012/0053491 A1 | 3/2012 | Nathan et al. |
| 2012/0191003 A1 | 7/2012 | Garabedian et al. |
| 2013/0123659 A1 | 5/2013 | Bartol et al. |
| 2013/0197321 A1 | 8/2013 | Wilson |
| 2013/0204097 A1 | 8/2013 | Rondoni et al. |
| 2013/0213659 A1 | 8/2013 | Luyster et al. |
| 2013/0253533 A1 | 9/2013 | Bartol et al. |
| 2014/0020178 A1 | 1/2014 | Stashuk et al. |
| 2014/0066803 A1 | 3/2014 | Choi |
| 2014/0088029 A1 | 3/2014 | Sugimoto et al. |
| 2014/0121555 A1 | 5/2014 | Scott et al. |
| 2014/0148725 A1 | 5/2014 | Cadwell |

(56) References Cited

U.S. PATENT DOCUMENTS

| | | |
|---|---|---|
| 2014/0163411 A1 | 6/2014 | Rea |
| 2014/0275926 A1 | 9/2014 | Scott et al. |
| 2014/0276195 A1 | 9/2014 | Papay et al. |
| 2014/0358026 A1 | 12/2014 | Mashiach et al. |
| 2015/0032022 A1 | 1/2015 | Stone et al. |
| 2015/0045783 A1 | 2/2015 | Edidin |
| 2015/0051506 A1 | 2/2015 | Wybo et al. |
| 2015/0051507 A1* | 2/2015 | Wybo .............. A61B 5/1109 600/554 |
| 2015/0112325 A1 | 4/2015 | Whitman |
| 2015/0230749 A1 | 8/2015 | Gharib et al. |
| 2015/0342521 A1 | 12/2015 | Narita et al. |
| 2015/0342621 A1 | 12/2015 | Jackson |
| 2016/0051812 A1 | 2/2016 | Montgomery, Jr. et al. |
| 2016/0121109 A1 | 5/2016 | Edgerton et al. |
| 2017/0347941 A1 | 12/2017 | Ejiri et al. |

FOREIGN PATENT DOCUMENTS

| | | |
|---|---|---|
| FR | 2920087 A1 | 2/2009 |
| WO | 0078209 A2 | 12/2000 |
| WO | 2007024147 A1 | 3/2007 |

OTHER PUBLICATIONS

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja D.M. Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference Biosignal 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

Anderson, Edward; Wybo, Christophe;, An analysis of agreement between MMG vs EMG systems for identification of nerve location during spinal procedures Spine Journal, Suppl. 10.9, 93S-94S Sep. 2010.

Bartol, Stephen; Wybo, Christopher; The use of Mechanomyography MMG to locate nerves during spine surgery procedures, Spine Journal, Suppl. 10.9, 128S, Sep. 2010.

\* cited by examiner

NEURAL EVENT DETECTION

TECHNICAL FIELD

The present disclosure relates generally to a surgical diagnostic system for detecting the presence of one or more nerves.

BACKGROUND

Traditional surgical practices emphasize the importance of recognizing or verifying the location of nerves to avoid injuring them. Advances in surgical techniques include development of techniques including ever smaller exposures, such as minimally invasive surgical procedures, and the insertion of ever more complex medical devices. With these advances in surgical techniques, there is a corresponding need for improvements in methods of detecting and/or avoiding nerves.

SUMMARY

A neural monitoring system is provided that is capable of detecting an artificially-induced mechanical response of a muscle to stimulus that is provided within an intracorporeal treatment area of a human subject. The intracorporeal treatment area generally includes a nerve that innervates the monitored muscle. The present system utilizes advanced filtering techniques to aid in discriminating an induced response from all other responses.

The neural monitoring system includes a non-invasive mechanical sensor, a stimulator, and a processor. The mechanical sensor is configured to be placed in mechanical communication with the muscle and is operative to generate a mechanomyography output signal that corresponds to a sensed mechanical movement of the muscle. The stimulator is configured to provide a periodic stimulus within the intracorporeal treatment area, where the periodic stimulus includes at least a first stimulus beginning at a first time ($T_1$), and a second, consecutive stimulus beginning at a second time ($T_2$).

The processor is in communication with both the mechanical sensor and the stimulator, and is operative to provide the periodic stimulus to the stimulator for the ultimate delivery to the intracorporeal treatment area, and to receive the mechanomyography output signal from the mechanical sensor. The processor may be configured to analyze a response window of the mechanomyography output signal to determine if the first stimulus induced a response of the muscle. If an induced response is detected, the processor may provide a corresponding indication to a user, such as in the form of an alert, sound, altered color on a coupled display, or the like. Conversely, if an induced response is not detected within the response window, the processor may provide a different indication to the user to indicate that the stimulus did not induce a muscular response. In one configuration, the response window corresponds to a period of time when an induced response to the first stimulus is likely to occur. This response window generally extends between a third time ($T_3$) and a fourth time ($T_4$) such that $T_1 \leq T_3 < T_4 < T_2$.

In some embodiments, the processor is configured to determine if the first stimulus induced a response of the muscle by examining one or more characteristics of the mechanomyography output signal within the response window using a supervised learning algorithm that is operative to classify the response window as being either representative of an induced response of the muscle, or not representative of an induced response of the muscle. In an embodiment, the supervised learning algorithm may include an image-based classifier operative to analyze one or more graphical aspects of a graph of the mechanomyography output signal.

In an embodiment, the mechanical sensor may be a tri-axis accelerometer operative to monitor acceleration in three mutually orthogonal axes. The processor may then be configured to determine if the first stimulus induced a response of the muscle using a magnitude of a resultant vector calculated from the monitored acceleration in each of the three axes. In some embodiments, the processor may be configured to only determine if the first stimulus induced a response of the muscle if a magnitude of a movement of the muscle in a direction normal to the skin surface is greater than a magnitude of a movement of the muscle in a direction that is tangential to the skin surface.

As an additional background removal filter, in an embodiment, the processor may be further configured to identify signal content from the mechanomyography output signal that exists at least partially outside of the response window; determine a frequency component of that signal content; and attenuate the frequency component from the mechanomyography output signal within the response window. This filtered response window may then be used to determine if the first stimulus induced a response of the muscle. In some embodiments, the signal content exists at least partially between $T_1$ and $T_2$. Likewise, in some embodiments, the signal content may exist across a plurality of stimuli.

In some embodiments, the processor may be configured to use techniques described herein to more accurately determine a change in muscle response latency or nerve conduction velocity. For example, the processor may be configured to identify a time corresponding to a detected induced muscle response within the response window; determine a first response latency between the first stimulus and the time corresponding to a detected induced muscle response; identify a time corresponding to a subsequently detected muscle response that is induced by a subsequent stimulus provided by the stimulator; determine a second response latency between the subsequent stimulus and the time of the subsequently detected muscle response; and provide an alert if the second response latency differs from the first response latency by more than a predetermined amount.

In some embodiments, the current magnitude of the applied stimulus may be controlled in a closed loop manner to identify the lowest current that induces a threshold response of the muscle. This may operate by examining a difference between the mechanomyography output signal magnitude and a threshold output signal magnitude, and attempting to minimize that difference using a model describing how the response corresponds to the muscle output.

A method of detecting an artificially-induced mechanical response of a muscle to a stimulus provided within an intracorporeal treatment area of a human subject includes: transmitting a periodic electrical stimulus to a stimulator within the intracorporeal treatment area, receiving a mechanomyography output signal from a non-invasive mechanical sensor in mechanical communication with the muscle, detecting motion from the received mechanomyography output signal, and providing an indication to a user that the motion is an artificially-induced muscle response only if the motion occurs within a response window that exists between a first stimulus and a second, consecutive stimulus.

The above features and advantages and other features and advantages of the present technology are readily apparent from the following detailed description when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

The present disclosure provides a neural monitoring system with improved capabilities for detecting an artificially-induced response of a muscle to a stimulus. More specifically, the processing techniques described herein enable a more robust event detection capability, while reducing the occurrence of false positives.

Figure 1:
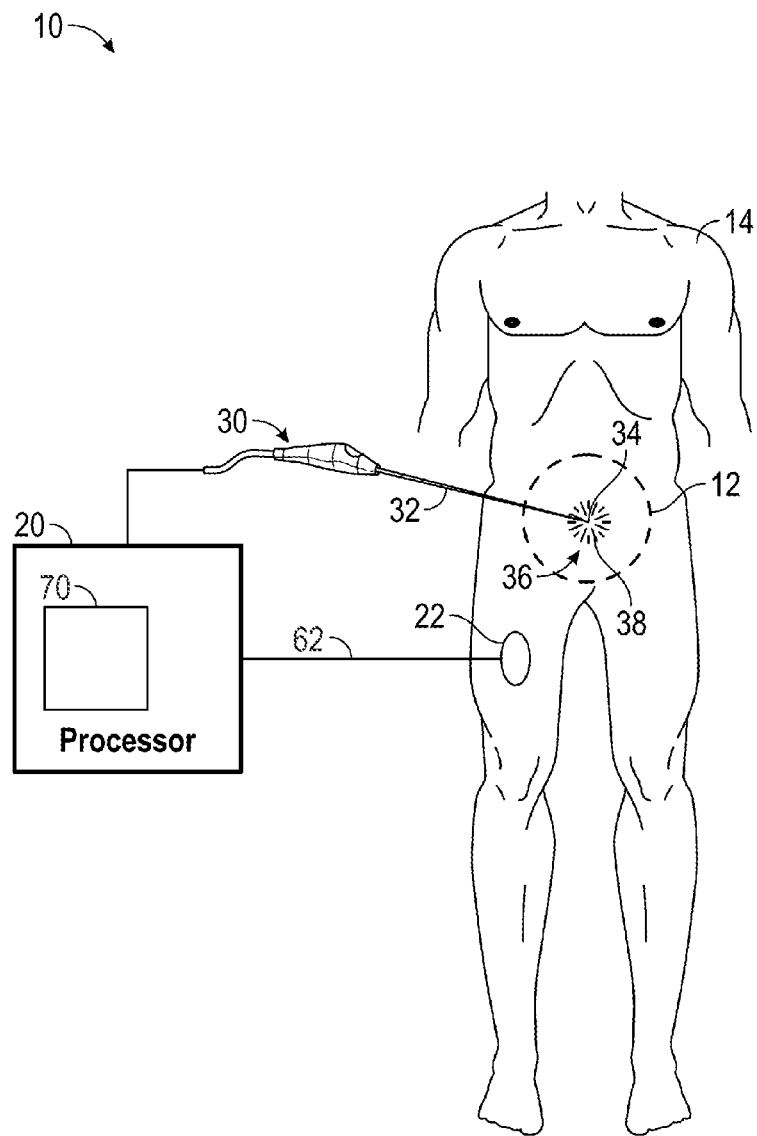
FIG. 1 is a schematic diagram of a neural monitoring system for detecting an artificially-induced mechanical muscle response.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14. As will be described in greater detail below, the system 10 may monitor one or more muscles of the subject 14 for a mechanical motion, and may be capable of discriminating an artificially-induced mechanical response of a muscle (also referred to as an "artificially-induced mechanical muscle response") from a subject-intended muscle contraction/relaxation and/or an environmentally caused movement. If an artificially-induced mechanical muscle response is detected during the procedure, the system 10 may provide an indication to a user.

As used herein, an artificially-induced mechanical muscle response refers to a contraction or relaxation of a muscle in response to a stimulus that is not received through natural sensory means (e.g., sight, sound, taste, smell, and touch). Instead, it is a contraction/relaxation of a muscle that is induced by the application of a stimulus directly to a nerve that innervates the muscle. Examples of stimuli that may cause an "artificially-induced" muscle response may include an electrical current applied directly to the nerve or to intracorporeal tissue or fluid immediately surrounding the nerve. In this example, if the applied electrical current is sufficiently strong and/or sufficiently close to the nerve, it may artificially cause the nerve to depolarize (resulting in a corresponding contraction of the muscle innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially-induced mechanical muscle response, a muscle innervated by the artificially depolarized nerve may physically contract or relax (i.e., a mechanical response). Such a mechanical reaction may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state, and is distinguished from other global translations of the muscle The neural monitoring system 10 may include a processor 20 that is in communication with at least one mechanical sensor 22. The mechanical sensor 22 may include, for example, a strain gauge, a force transducer, a position encoder, an accelerometer, a piezoelectric material, or any other transducer or combination of transducers that may convert a physical motion into a variable electrical signal.

Each mechanical sensor 22 may be specially configured to monitor a local mechanical movement of a muscle of the subject 14. For example, each sensor 22 may include a fastening means, such as an adhesive material/patch, that allows the sensor 22 to be adhered, bandaged, or otherwise affixed to the skin of the subject 14 (i.e. affixed on an external skin surface). Other examples of suitable fastening means may include bandages, sleeves, or other elastic fastening devices that may hold the sensor 22 in physical contact with the subject 14. Alternatively, the mechanical sensor 22 (and/or coupled device) may be configured to monitor a local mechanical movement of a muscle by virtue of its physical design. For example, the sensors/coupled devices may include catheters, balloons, bite guards, orifice plugs or endotracheal tubes that may be positioned within a lumen or natural opening of the subject to monitor a response of the lumen or orifice, or of a muscle that is directly adjacent to and/or connected with the lumen or orifice. In one configuration, the mechanical sensor may be a non-invasive device, whereby the term "non-invasive" is intended to mean that the sensor is not surgically placed within the body of the subject (i.e., via cutting of tissue to effectuate the placement). For the purposes of this disclosure, non-invasive sensors may include sensors that are placed within naturally occurring body lumens that are accessible without the need for an incision.

In one configuration, the sensor 22 may include a contact detection device, that may provide an indication if the sensor 22 is in physical contact with the skin of the subject 14. The contact detection device may, for example, include a pair of electrodes that are configured to contact the skin of the subject 14 when the sensor 22 is properly positioned. The sensor 22 and/or contact detection device may then monitor an impedance between the electrodes to determine whether the electrodes are in contact with the skin. Other examples of suitable contact detection devices may include capacitive touch sensors or buttons that protrude slightly beyond the surface of the sensor.

The system 10 may further include one or more elongate medical instruments 30 that are capable of selectively providing a stimulus within the intracorporeal treatment area 12 of the subject 14 (i.e., also referred to as a stimulator 30). For example, in one configuration, the elongate medical instrument 30 may include a probe 32 (e.g., a ball-tip probe, k-wire, or needle) that has an electrode 34 disposed on a distal end portion 36. The electrode 34 may be selectively electrified, at either the request of a user/physician, or at the command of the processor 20, to provide an electrical stimulus 38 to intracorporeal tissue of the subject. In other configurations, the elongate medical instrument 30 may include a dilator, retractor, clip, cautery probe, pedicle screw, or any other medical instrument that may be used in an invasive medical procedure. Regardless of the instrument, if the intended artificial stimulus is an electrical current, the instrument 30 may include a selectively electrifiable electrode 34 disposed at a portion of the instrument that is intended to contact tissue within the intracorporeal treatment area 12 during a procedure.

During a surgical procedure, the user/surgeon may selectively administer the stimulus to intracorporeal tissue within the treatment area 12 to identify the presence of one or more nerve bundles or fibers. For an electrical stimulus 38, the user/surgeon may administer the stimulus, for example, upon depressing a button or foot pedal that is in communication with the system 10, and more specifically in communication with the stimulator 30. The electrical stimulus 38 may, for example, be a periodic stimulus that includes a plurality of sequential discrete pulses (e.g., a step pulse) provided at a frequency of less than about 10 Hz, or from about 1 Hz to about 5 Hz, and preferably between about 2 Hz and about 4 Hz. Each pulse may have a pulse width within the range of about 50 µs to about 400 µs. In other examples, the discrete pulse may have a pulse width within the range of about 50 µs to about 200 µs, or within the range of about 75 µs to about 125 µs. Additionally, in some embodiments, the current amplitude of each pulse may be independently controllable.

If a nerve extends within a predetermined distance of the electrode 34, the electrical stimulus 38 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, the impedance between the electrical stimulus and the ground patch, and the magnitude of the stimulus current. In one configuration, a lookup table may be employed by the processor 20 to provide an approximate distance between the electrode and the nerve, given a known stimulus magnitude and a measured mechanical muscle response.

Prior to beginning a surgical procedure, the one or more mechanical sensors 22 may be placed in mechanical communication with one or more muscles of the subject 14. In the present context, a sensor 22 may be in mechanical communication with the muscle if it can physically detect a movement, velocity, acceleration, strain or other physical response of the muscle, either via direct contact with the muscle, or via a mechanical relationship through one or more intermediate materials and/or tissues (e.g., skin and/or subcutaneous tissue).

Figure 2:
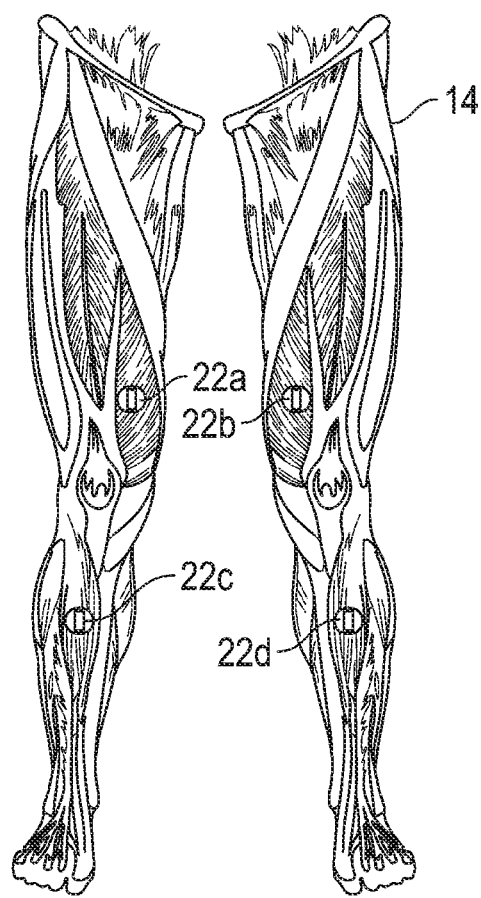
FIG. 2 is a schematic front view of the placement of a plurality of mechanical sensors on the legs of a subject.
Figure 3:
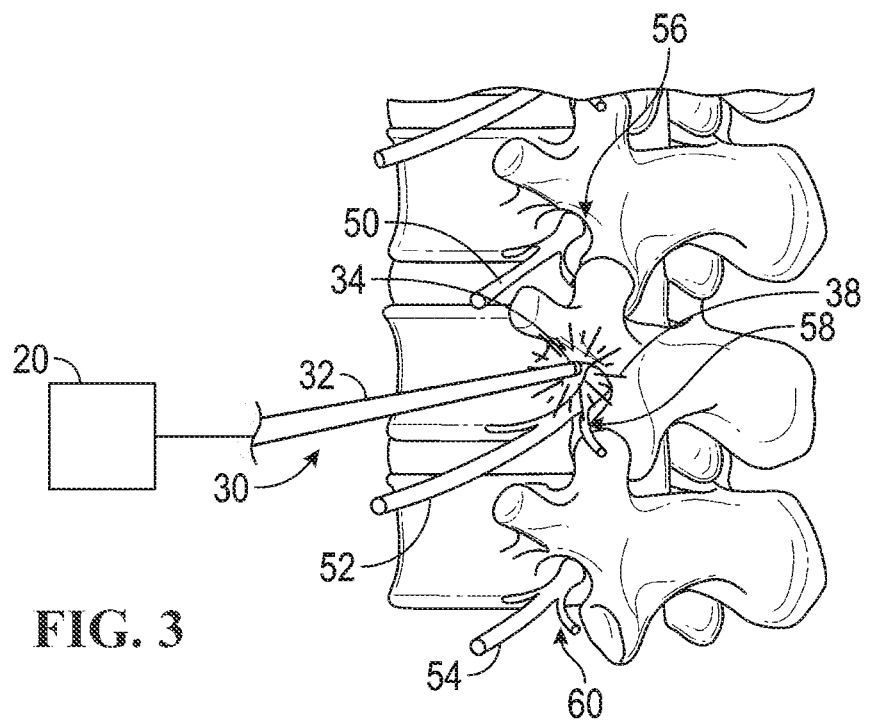
FIG. 3 is a schematic side view of an intracorporeal treatment area including a portion of the lumbar spine.

FIG. 2 illustrates an example of the placement of a plurality of mechanical sensors 22 for a surgical procedure that may occur proximate the L2, L3, and/or L4 vertebrae of the lumbar spine (shown schematically in FIG. 3). The nerves 50, 52 and 54 exiting the L2, L3 and L4 foramen 56, 58, 60 may therefore either lie within the treatment area 12 (i.e., the area surrounding the L2, L3, and/or L4 vertebrae), or may be immediately proximate to this area. Using common anatomical knowledge, the surgeon may understand that damage to these nerves 50, 52, 54 may affect the functioning of the vastus medialis muscles and the tibialis anterior muscles. As such, the surgeon may place mechanical sensors 22a-22d on or near the vastus medialis muscles and the tibialis anterior muscles to guard against inadvertent manipulation of the nerves during the procedure. For example, mechanical sensors 22a and 22b are placed on the vastus medialis muscles, which are innervated by the nerves 50, 52 exiting the L2 and L3 foramen 56, 58, and sensors 22c and 22d are placed on the tibialis anterior muscles, which are innervated by the nerves 54 exiting the L4 foramen 60.

In general, each mechanical sensor 22 may generate a mechanomyography (MMG) output signal (schematically shown at 62) that corresponds to a sensed mechanical movement/response of the adjacent muscle. The MMG output signal 62 may be either a digital or analog signal, and the sensor 22 may further include communication circuitry operative to transmit the mechanomyography output signal to the processor through a wired or wireless communication protocol (e.g., through one or more wired data transmission protocols operative to communicate data over a physical wire such as I2C, CAN, TCP/IP, or other wired protocols; or through the use of one or more wireless/radio frequency-based data transmission protocols, such as according to IEEE 802.11, Bluetooth, ZigBee, NFC, RFiD or the like). As a specific signal, the MMG output signal 62 is intended to be separate and distinct from any electrical potentials of the muscle or skin (often referred to as electromyography (EMG) signals). While electrical (EMG) and mechanical (MMG) muscle responses may be related, their relationship is complex, and not easily described (e.g., electrical potentials are very location specific, with a potentially variable electrical potential across the volume of the muscle of interest).

Referring again to FIG. 1, the processor 20 may be in communication with the stimulator 30 and the mechanical sensor 22, and may be configured to receive the MMG output signal 62 from the mechanical sensor 22. The processor 20 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

The processor 20 may be configured to automatically perform one or more signal processing algorithms 70 or methods to determine whether a sensed mechanical movement (i.e., via the MMG output signal 62) is representative of an artificially-induced mechanical muscle response or if it is merely a subject-intended muscle movement and/or an environmentally caused movement. These processing algorithms 70 may be embodied as software or firmware, and may either be stored locally on the processor 20, or may be readily assessable by the processor 20.

Figure 4:
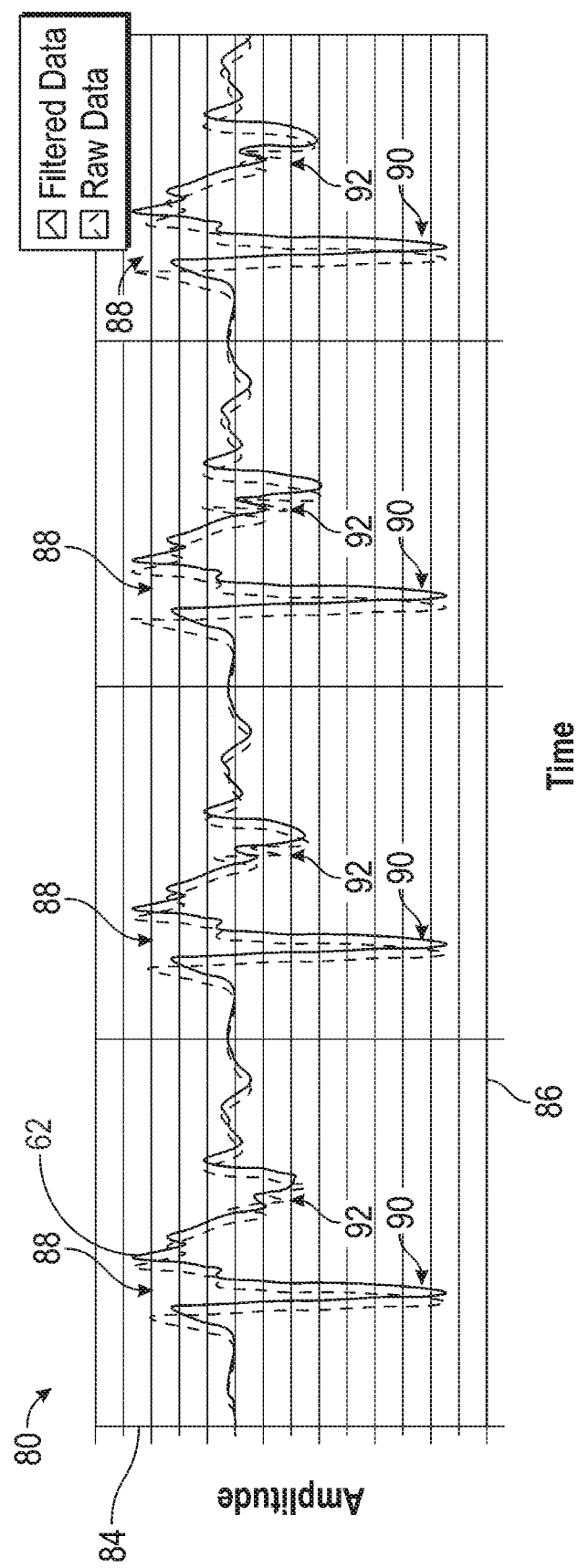
FIG. 4 is a schematic time-domain graph of a mechanomyography output signal in response to a periodic electrical stimulus.

FIG. 4 generally illustrates a graph 80 of an MMG output signal 62 in response to a periodic electrical stimulus 38 provided proximate to a nerve. It should be noted that the graph 80 is provided for illustrative purposes to show a generalized muscular response to a periodic stimulus provided at about a 3 Hz stimulation frequency. As shown, the MMG output signal 62 has an amplitude 84 that varies as a function of time 86 and includes a plurality of generally discrete contraction events 88. Each contraction event 88 may include, for example, an initial response 90 (e.g., an M-wave), and a plurality of subsequent peaks/valleys 92 (e.g., an H-reflex).

Figure 5:
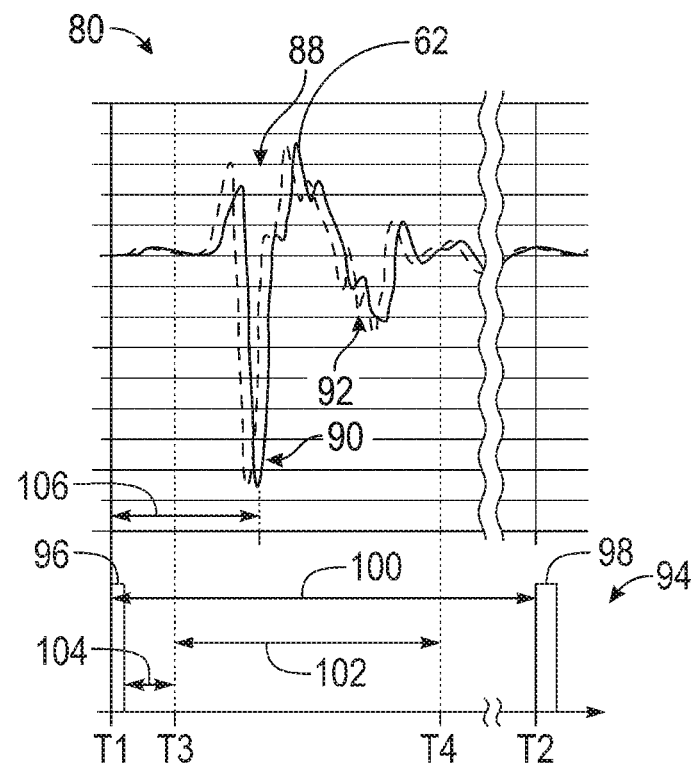
FIG. 5 is a schematic time-domain graph of an induced mechanical response of a muscle within a response window that exists after the application of an inducing stimulus.

FIG. 5 provides an enlarged view of the first event 88 of FIG. 4. In addition to the graph 80 of the MMG output signal 62, FIG. 5 additionally includes a graph 94 representing two consecutive stimuli 96, 98. As generally shown, the first stimulus 96 may be provided by the stimulator beginning at a first time, $T_1$. The second, consecutive stimulus may be provided by the stimulator beginning at a second time, $T_2$. The length of time 100 between $T_1$ and $T_2$ may also be regarded as the period 100 of the periodic stimulus 38. This period 100 may typically be between about 100 ms and 1000 ms, or more typically between about 250 ms and about 500 ms. Within the length of time 100 following the first stimulus 96, there may be a narrower window of time where a muscle event 88 is most likely to occur in response to the first stimulus 96 (i.e., the "response window 102"). The response window 102 generally begins at a time $T_3$ that is on or shortly after $T_1$ and that may represent the earliest time where a response of the muscle to the stimulus could be expected. Likewise, the response window 102 generally ends at a time $T_4$ that is before the next stimulus 98 begins and that provides a large enough period of time from $T_3$ to include at least the entire initial response 90, if one were to occur.

The offset 104 between $T_1$ and $T_3$, if one were to exist would be minimal, as the delay between stimulation and the initial muscle response 90 is only limited by the speed at which the nerve signal propagates, the length of the nerve, and the dynamics of the muscle to actually contract in response to the nerve signal. In most patients, motor nerves can conduct generally between about 40 m/s and about 80 m/s, which could result in about a 5-20 ms delay until the start of the muscular contraction. In some embodiments, the start time $T_3$ of the response window 102 could be further refined by accounting for specific attributes of the patent, such as body mass index (BMI), diabetes, neuropathy, degenerative nerve conditions, or other such factors that are known to affect nerve conduction velocity and/or muscular response.

The relative location of $T_4$ within the period 100 may generally be selected such that if a muscle event 88 were to occur in response to the first stimulus 96, a sufficient amount of information related to the event would fall within the response window 102 to properly categorize it as an induced/evoked muscle response. This later bound may generally depend on the amount of time 106 between $T_1$ and the initial onset and/or peak of the muscle response, as well as on the expected duration of the event 88. From a clinical perspective, it is most important that $T_3$ and $T_4$ are selected to capture at least the initial M-wave response 90 within the response window 102. Similar to $T_3$, the offset of $T_4$ relative to $T_1$ may be further refined by accounting for specific attributes of the patient, such as body mass index (BMI), diabetes, neuropathy, degenerative nerve conditions, muscle fatigue, or other such factors that are known to affect nerve conduction velocity and/or muscular response.

Properly sizing the response window 102 within the period 100 between the stimuli may enable the processor 20 to summarily reject some muscle events (or other detected movements) if those events occur outside of the expected response window 102. For example, if a periodic stimulus was applied to a subject at a frequency of 2 Hz (500 ms period), any given pulse may be expected to elicit a response within about the first 100 ms of the onset of the pulse (i.e., with slight variability based on the health of the patient). If a purported muscle event 88 was detected in the later 400 ms of the period 100, it may be safe to assume that the applied stimulus did not cause that motion.

Using these assumptions, in one embodiment, the processor 20 may be configured to only perform the signal processing algorithms 70 on sensed motion or muscle events that occur within the response window 102. Such a time-gating filter may reduce the total number of potential events that must be analyzed, which may conserve processing power, improve processing speed, and reduce the potential for false positives. As mentioned above, the response window should be sized such that $T_1 \leq T_3 < T_4 < T_2$, however, to best realize the processing improvements, it is preferable for $(T_4-T_3) \leq (T_2-T_1)/2$.

In some embodiments, the signal processing algorithms 70 may involve one or more analog detection techniques such as described, for example, in U.S. Pat. No. 8,343,065, issued on Jan. 1, 2013 (the '065 Patent), which is incorporated by reference in its entirety, and/or one or more digital detection techniques, such as described in US 2015/0051506, filed on Aug. 13, 2013 (the '506 Application), which also is incorporated by reference in its entirety. In the analog techniques, the processor 20 may examine one or more aspects of the MMG output signal 62 in an analog/time domain to determine if the sensed response is an artificially-induced response of the muscle to the stimulus. These analog aspects may include, for example, the time derivative of acceleration, or the maximum amplitude of the M-wave/initial response 90.

In a digital context, such as described in the '503 Application, the processor 20 may compare the frequency components of the MMG output signal (i.e., in the frequency domain) with the frequency of the applied stimulation to determine whether the sensed muscle responses and/or "events" were induced by the applied stimulus. Such a technique may be made more robust by considering only events or muscle activity that occurs within the reference window 102 and/or by aggressively filtering/attenuating or ignoring the signal outside of the response window 102 prior to applying the signal processing algorithms 70.

In some embodiments, the signal processing algorithms 70 may include one or more supervised learning algorithms that are operative to classify any sensed motion into one of a plurality of classifications that include at least whether the signal 62 is, or is not representative of an artificially-induced mechanical response of the muscle. Both classifications may provide valuable information to an operating surgeon during a procedure. Affirmatively detecting a response informs the surgeon that a nerve is proximate to the stimulator/tool, and to proceed with caution. Conversely, determining that no induced response occurred, particularly if a stimulus is provided, informs the surgeon that the nerve is not present and they can proceed in their normal manner.

In a general sense, a supervised learning algorithm is an algorithm that attempts to classify a current sample using observations made about prior samples and their known classifications. More specifically, the algorithm attempts to construct and/or optimize a model that is capable of recognizing relationships or patterns between the training inputs and training outputs, and then the algorithm uses that model to predict an output classification given a new sample. Examples of supervised learning algorithms that may be employed include neural networks, support vector machines, logistic regressions, naive Bayes classifiers, decision trees, random forests, or other such techniques or ensembles of techniques.

Figure 6:
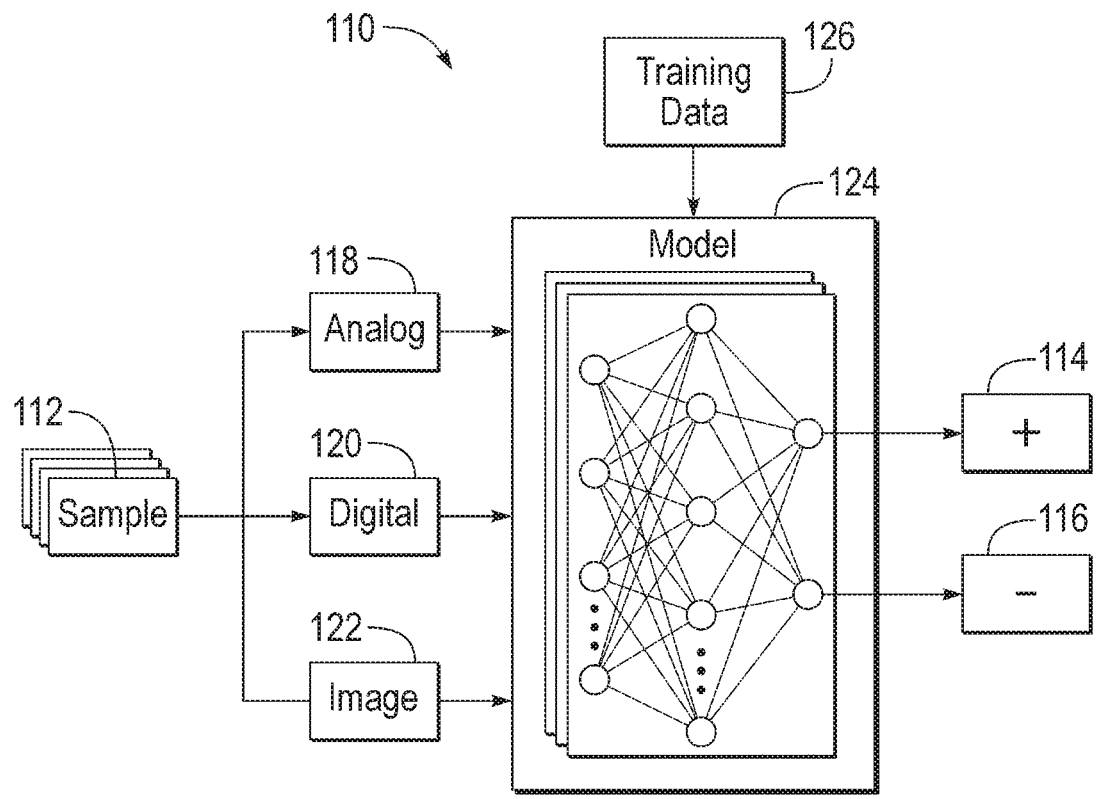
FIG. 6 is a schematic diagram of a signal processing algorithm, including a supervised learning algorithm, for classifying a sensed muscle motion as being either an induced response or not an induced response.

FIG. 6 schematically illustrates an embodiment of a supervised learning algorithm 110 that may be used to classify a current sample 112 of an MMG output signal 62 into a binary classification (i.e., an artificially induced muscle response 114, or not an artificially induced response 116). As shown, the processor 20 may initially characterize the MMG output signal 62 and/or recognized muscle event (i.e., any sensed motion relative to a baseline) according to one or more analog characteristics 118, frequency characteristics 120, and/or time-series/image characteristics 122. Using a model 124 constructed/optimized on the basis of a plurality of pre-classified training samples 126, the supervised learning algorithm 110 may then make an informed classification that minimizes an established error function or maximizes the probability of an accurate prediction.

In an embodiment, the one or more analog characteristics 118 may include, for example, max/min acceleration amplitudes, max/min velocity amplitudes, time derivative of acceleration, signal rise time, or curve fitting coefficients. Likewise, the one or more frequency characteristics 120 may include, for example, FFT coefficients, peak frequencies, peak frequency magnitudes, harmonic frequencies, or frequency fall-off. Finally, the time-series/image characteristics 120 may include a snapshot of a graph 80 of the MMG output 62 over time (similar to what is shown in FIG. 5). In general, as discussed in the '065 Patent and in the '506 Application, artificially-induced muscle responses have certain analog and frequency characteristics that non-induced responses do not. As such, the supervised learning algorithm 110 may model these characteristics 118, 120 in the aggregate to predict the nature of the muscle event with a greater accuracy. Furthermore, in some situations, the visual attributes of an induced response may tell a more complete story than any one parameter or collection of parameters could. As such, in an embodiment, the supervised learning algorithm 110 may include an image based classifier that may attempt to classify a muscle response on the basis of a visual similarity with other previously identified induced responses.

In some embodiments, the supervised learning algorithm 110 may employ an ensemble approach to generating the output classification. In such an approach, the model 124 may include a plurality of different models/approaches that may be combined according to a weighting/costing formula to provide improved redundancy/voting. In another embodiment, the ensemble approach may use the output of one or more approaches/models as an input of another model. For example, the analog and/or frequency based detection techniques discussed in the '065 Patent and/or in the '506 Application may output a probability or likelihood that an event in question is representative of an induced response. These estimations may then be fed into, for example, a supervised learning algorithm as another input (i.e., where the supervised learning algorithm may understand situations when the pre-determined algorithms are to be trusted or not trusted). In another embodiment, each model, including any supervised learning algorithm may feed into a separate algorithm that may output a binary response or probability based upon the outcomes of the various models. This approach may use voting algorithms, probability combinations, and/or separate supervised learning algorithms to provide an output based on the prediction of each constituent model.

While each of the above-referenced signal processing algorithms 70 may alone, or in combination, provide reliable detection functionality, in some embodiments, the detection functionality may be made more robust by using one or more techniques to increase the signal to noise ratio of the MMG output signal 62. In a general sense, the signal-to-noise ratio represents how recognizable a muscle event is when occurring amidst other sensed movement, signal noise, or other occurrences within the operating room. Already, MMG technology provides a vastly improved signal-to-noise ratio from previously used EMG technology, however, further improvements are still available.

In one embodiment, the time gating approach that is reliant on the response window 102 may be used to identify and remove background noise with a higher degree of confidence than might be performed in a continuous monitoring approach. More specifically, activity that at least partially occurs outside of the response window 102 may be assumed to not have been caused by the applied stimulus, and thus may be classified as "background noise" when attempting to identify an induced muscle response. Furthermore, it may be assumed that signal content occurring across a plurality of stimuli is also not representative of an artificially induced muscle response since an induced response tends to settle out prior to the application of the next sequential stimulus. Therefore, in some embodiments, activity that occurs at least partially outside of the reference window 102 may be viewed as noise (to the induced-response detection algorithms 70) and used to tune a digital filter. This filter may then be applied to the signal prior to any of the signal processing algorithms 70 described above.

Figure 7:
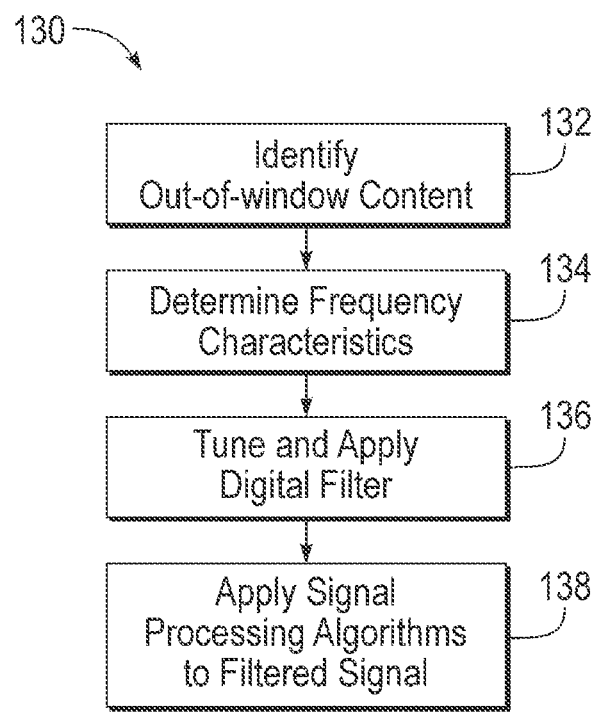
FIG. 7 is a schematic flow diagram of a method of removing background noise that occurs at least partially outside of the response window.

FIG. 7 schematically illustrates a method 130 of removing background noise that occurs at least partially outside of the response window 102. This method 130 begins at 132 by identifying signal content from the mechanomyography output signal 62 that exists at least partially outside of the response window 102. In some embodiments, the processor 20 may identify this signal content, for example, by converting the mechanomyography output signal 62 into the frequency domain (e.g. via a fast Fourier transform), and searching for signal content having a period (i.e., inverse of frequency) that is greater than the length of the response window 102 and/or having a frequency that is less than about the frequency of the applied stimulus. This signal content may represent motion that may extend across a plurality of stimuli/response windows and therefore is at least partially outside of any given response window 102. Alternatively, or additionally, the processor 20 may search for signal content with a faster frequency that appears in both a response window 102 and an adjacent period of time outside of the response 102. While it is preferable for each response window 102 to be filtered using content that at least partially exists in a directly adjacent period of time outside of that response window, in some embodiments, the signal content may be previously detected and recognized to occur on a recurring basis (e.g., a 10 Hz signal occurring on a 0.1 Hz period, or a half-wave rectified signal).

The processor 20 may then determine a frequency characteristic of this signal content, for example, using a fast Fourier transform (FFT) at 134. Frequency characteristics may include an identification of the dominant frequencies, harmonics, phase angles, etc.

Once this out-of-window content is identified, its frequency and phase may be used to tune a digital filter to attenuate this frequency content from the mechanomyography output signal 62 within at least the response window 102 (at 136). This cleaned up response window may then be passed to the one or more signal processing algorithms 70 (at 138), which may be used to determine the occurrence of an artificially-induced response of the muscle.

As may be appreciated, this background identification and removal technique may improve signal-to-noise ratio of the MMG output signal 62 by reducing the noise (i.e., the denominator). In some embodiments, the signal-to-noise ratio may also be improved using techniques that improve the quality of the signal during an event (i.e., the numerator). In one embodiment, the quality of the signal may be improved through the use of an MMG sensor 22 that is capable of sensing motion in three orthogonal axes (i.e. a "tri-axis mechanical sensor").

In an embodiment, one or more of the mechanical sensors 22 described above may be a tri-axis mechanical sensor that is specially configured to monitor a local mechanical movement of a muscle of the subject 14 in three orthogonal axes. In a first configuration, the sensed motion from each of the three axes may be independently fed into the signal processing algorithms 70. In doing so, the algorithms 70 may have more information about the event upon which they can base their classification. This technique may be particularly useful with the supervised learning algorithms 110, which may identify patterns between the various channels that are indicative of an induced muscle response.

In some embodiments, the sensed motion in each of the three orthogonal axes may be combined to form a resultant vector that more accurately describes the magnitude and direction of the sensed response. More specifically, the resultant vector will always have a magnitude that is greater than or equal to the magnitude of any one axis; and, with the larger magnitude comes a greater signal. As an additional benefit, the use of a tri-axis mechanical sensor may reduce any signal variance/error that is attributable to improper sensor placement. For example, if a sensor is not generally centered on a muscle group, the sensed motion may include some component that is tangential to the skin surface (i.e., where the contracting of the muscle causes off-center portions of the skin to rotate inward or outward while the central region may move in a substantially normal direction).

As an additional filtering technique, in one configuration, the resultant vector and/or any constituent vectors may only be considered by the signal processing algorithms 70 only if the magnitude of the sensed motion normal to the skin surface is greater than the sensed motion in any one axis that is tangential to the skin surface (and/or greater than the resultant vector formed between the two tangential axes). Such a filtering technique is premised on the understanding that an induced muscle response is primarily represented by motion in a direction normal to the skin surface. If the sensed motion tangential to the skin surface is too large relative to the motion normal skin, then there is a high probability that the sensed motion is not an induced muscle response, and therefore may be disregarded. In an embodiment, the sensed motion may be disregarded unless the magnitude of the normal motion is more than twice the magnitude of the resultant tangential motion. In other embodiments, the sensed motion may be disregarded unless the magnitude of the normal motion is more than three times, or four times, or even five times the magnitude of the resultant tangential motion.

Following the filtering and performance of the one or more signal processing algorithms 70, if the processor 20 concludes that a sensed motion and/or muscle event is an artificially-induced muscle response, then the processor 20 may provide an indication to a user corresponding to the detected event. In one configuration, this indication may include one or more of an illuminated light/LED, a colored light/LED, a textual or symbolic alert on a display device associated with the processor 20, a vibration in the handle of the stimulator, and an audible alert such as a single frequency alert, a multiple frequency alert, and/or an audible natural language alert. Moreover, the indication/alert may include an estimation of the proximity between the electrode and the nerve, such as may be derived using a lookup table as described above, or as explained in U.S. Pat. No. 8,343,065 to Bartol, et al., entitled "NEURAL EVENT DETECTION," which is hereby incorporated by reference in its entirety and for all of the disclosure set forth therein.

In addition to simply detecting an artificially induced muscle response, in an embodiment, the processor 20 may further be configured to examine the timing between a provided stimulus and a muscle response induced by this stimulus. If this timing changes by more than the threshold amount, the processor 20 may provide an alert to a user to indicate a change in the health of the nerve that innervates the responding muscle. As a general premise, nerve conduction velocity and/or muscle response latency should be faster with a healthy nerve than with an injured or impinged nerve.

Figure 8:
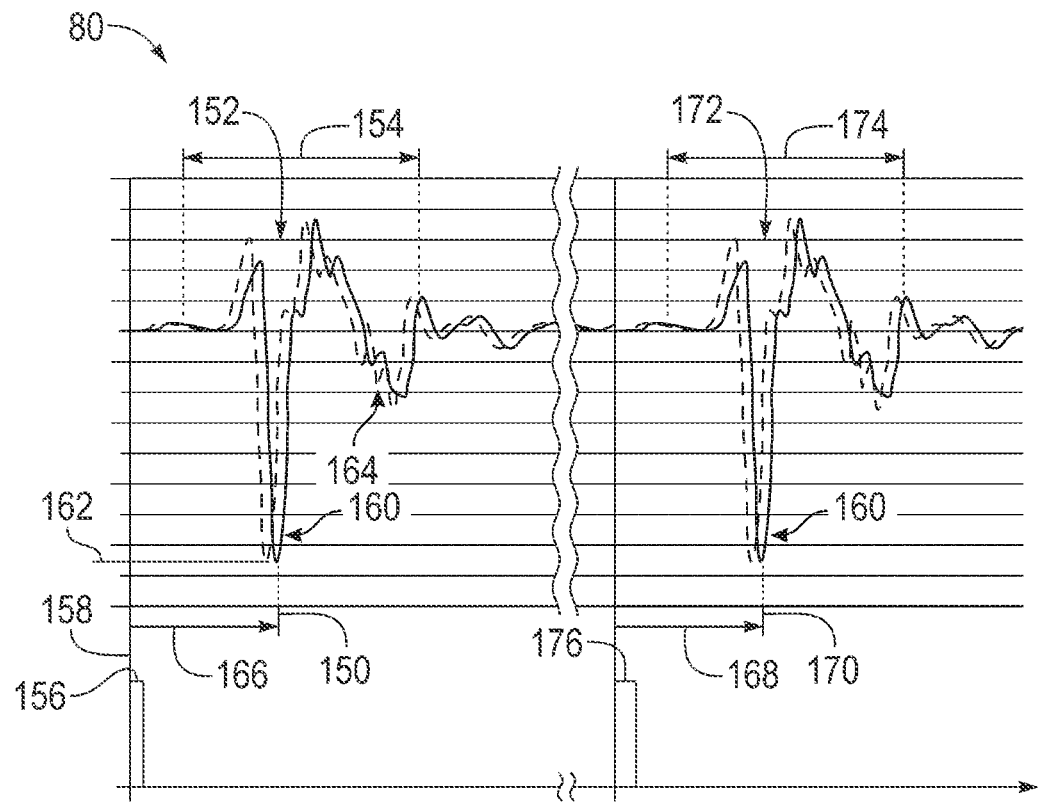
FIG. 8 is a schematic time-domain graph of a technique for comparing a latency between the application of a stimulus and the occurrence of an induced response occurring within a response window.

Therefore, as generally illustrated in FIG. 8, in an embodiment, the processor 20 may be configured to identify a time 150 of a first muscle event 152 that occurs within a first response window 154. The first muscle event 152 is induced by a first stimulus 156 that begins at the first time 158. As generally shown, the muscle event includes an initial M-wave response 160 having a peak magnitude 162, followed by later responses 164 such as the H-reflex. The processor 20 may be configured to determine a first response latency 166 between the first time 156 and the time 150 of the muscle event 152. While it is not critical where the time of the stimulus is recorded, it important that the latency 166 is consistently recorded between measurements. As such, the most optimal times to log the time of the stimulus is on either the rising or falling edge, and the most optimal time to log the time of the event is at the maximum peak (i.e., as peak detection techniques are easily implemented).

Once a baseline latency is established, either by computing a single latency, or an average of many successively computed latencies, future latencies (e.g., subsequent latency 168) may be computed in a similar manner and compared to the baseline. More specifically, the processor 20 may be configured to identify a time 170 of a second muscle event 172 within a second response window 174 following a subsequent stimulus 176 provided by the stimulator. The processor 20 may determine the response latency 168 between the stimulus 176 the second muscle event 172, and may then provide an alert if the second response latency 168 differs from the baseline latency by more than a predetermined threshold amount that is set to indicate either a meaningful improvement in the health of the nerve, or a meaningful impairment of the nerve. Additionally, or alternatively, the system 10 may display a constant readout that compares the nerve conduction velocity and/or muscle response latency to either a baseline level measured from that patient, or to a standard or expected velocity/latency, from which changes throughout the procedure can be gauged.

In an embodiment, the processor 20 may be configured to provide the electrical stimulus 38, via the stimulator, with a varying current magnitude that is a function of a difference between the maximum amplitude of the sensed M-wave response, and a threshold amplitude (alternatively, the current magnitude is a function of the difference between a sensed peak MMG output signal magnitude and a threshold MMG output signal magnitude).

Figure 9:
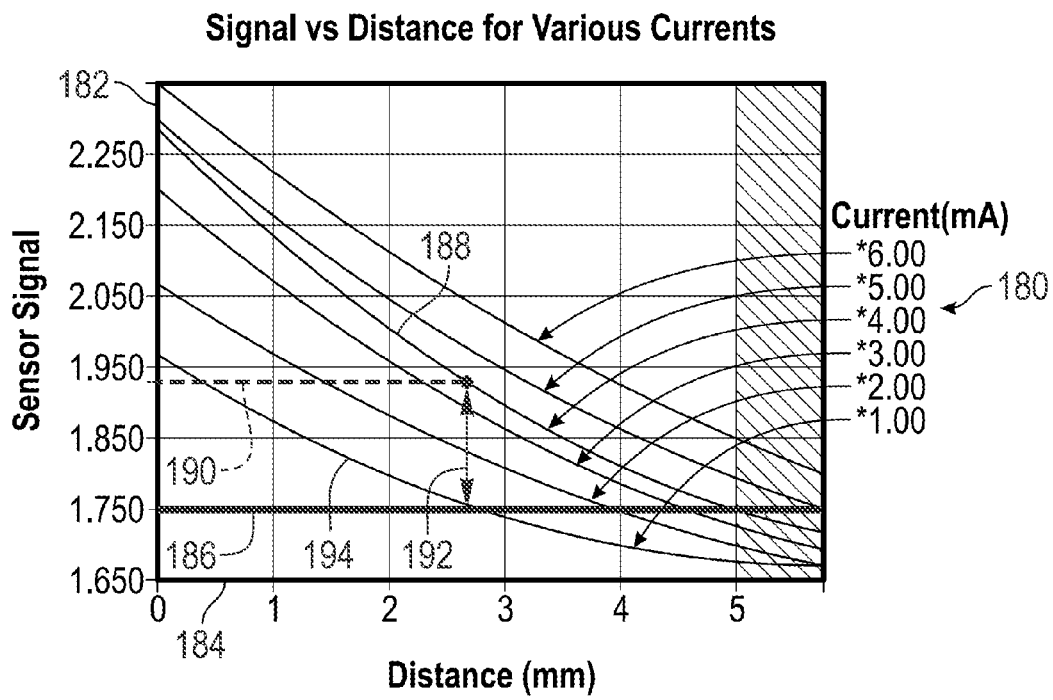
FIG. 9 is a schematic graph illustrating a stimulus current control algorithm that adjusts stimulus current on the basis of a relationship between a stimulus current, a sensor output signal magnitude, and a distance between the stimulator and a nerve.

In some surgical techniques, it may be useful for a surgeon to understand what is the minimum current amplitude of a an electrical stimulus 38 provided by the stimulator 30 to elicit a mechanical response that is greater than or equal to a predetermined threshold response. FIG. 9 illustrates an example of a graph that represents the relationship between current magnitude 180, MMG output signal (peak) magnitude 162, the distance 184 between the stimulator 30 and the nerve, and the threshold 186 response sought. If the processor 20 applies a stimulus at a known first current 188, which elicits a first MMG output magnitude 190, then the known relationships may enable the processor to use various closed-loop control techniques (e.g., various combinations of proportional, derivative, and integral control methods) to minimize the difference 192 between the sensed magnitude 190 and the threshold 186. In this example, such a closed loop control scheme would eventually arrive at a reduction of the current to the second level 194.

This closed-loop threshold hunting technique is highly dependent on an accurate model and the ability to get a consistent output signal from the sensor, which both exist using MMG technology (though are not generally possible with noisier signals such as may exist with other sensing methodologies such as EMG technology).

While the control technique generally illustrated in FIG. 9 assumes a stationary stimulator (i.e., the distance 184 does not change between the first and second current levels 188, 194, in another embodiment, the motion of the stimulator 30 may be tracked in an effort to approximate changes in distance between the stimulator and the nerve. The motion of the stimulator 30 may be tracked, for example, by including an accelerometer, inertial measuring unit, and/or gyroscope on the stimulator 30 or stimulator handle. Likewise, the motion of the stimulator 30 may be known if the stimulator is robotically controlled, or is sensed through another non-contact positioning technique. While motion of the stimulator is important, ultimately the control technique must understand motion of the stimulator relative to the nerve. Therefore, in some embodiments, the system may employ nerve detection and mapping techniques such as described in U.S. Patent Application No. 2017/0020611, filed on Oct. 5, 2016, which is incorporated by reference in its entirety.

Figure 10:
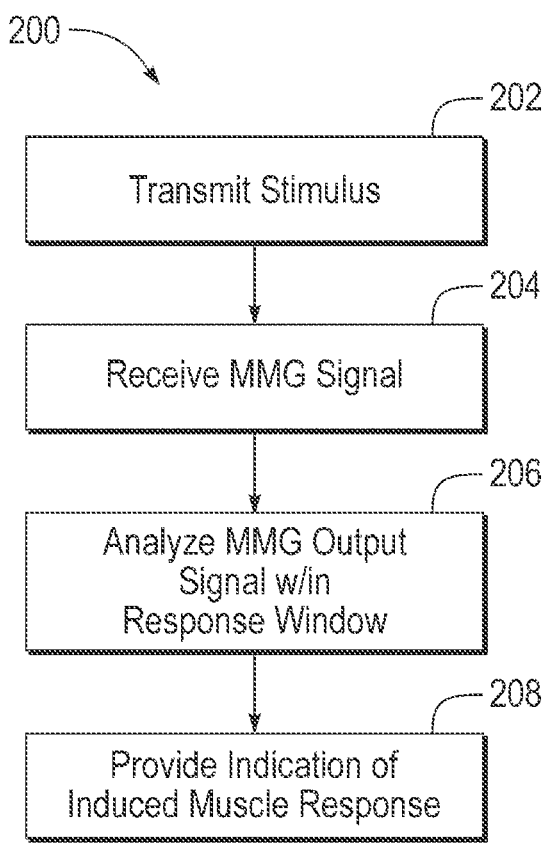
FIG. 10 is a schematic flow diagram of a method of detecting an artificially-induced mechanical response of a muscle to a stimulus provided within an intracorporeal treatment area of a human subject.

FIG. 10 schematically illustrates a method 200 of detecting an artificially-induced mechanical response of a muscle to a stimulus provided within an intracorporeal treatment area of a human subject. In general, the method 200 begins with the processor 20 transmitting a periodic electrical stimulus to a stimulator within the intracorporeal treatment area (at 202). Similar to that described above, the periodic stimulus includes at least a first stimulus beginning at a first time ($T_1$), and a second, consecutive stimulus beginning at a second time ($T_2$).

Concurrently with the transmission of the stimulus, the processor 20 may be receiving a mechanomyography output signal from one or more non-invasive mechanical sensors in mechanical communication with one or more muscles of the subject (at 204). The processor 20 may analyze the mechanomyography output signal (at 206) specifically within a response window that corresponds to a period of time when an induced response of the muscle to the first stimulus is likely to occur. The response window may extend between a third time ($T_3$) and a fourth time ($T_4$) such that $T_1 \leq T_3 < T_4 < T_2$.

In some embodiments, the step of analyzing the mechanomyography output signal within the response window may include performing one or more signal processing algorithms 70 on the sensed MMG output signal. In one embodiment, these signal processing algorithms 70 may be performed only if the motion occurs within the response window. In one embodiment, the signal processing algorithms 70 may include a supervised learning algorithm that examines one or more characteristics of the MMG output signal within the response window to determine if the sensed motion is an artificially-induced muscle response. The supervised learning algorithm may generally be operative to classify the motion into one of a plurality of classifications that include either that the sensed motion (and/or response window as a whole) is representative of an induced muscle response, or that the sensed motion (and/or response window) is not representative of an induced muscle response.

In some embodiments, the signal processing algorithms 70 may be performed on a "cleaned" signal that has background noise dynamically reduced or attenuated. Such a cleaning process my include identifying signal content from the mechanomyography output signal that exists at least partially outside of the response window; determining a frequency component of the signal content; and attenuating the frequency component from the mechanomyography output signal within the response window.

At step 208, the processor 20 may then provide an indication to a user that the sensed motion was an artificially-induced muscle response only if the motion occurs within the response window.

In addition to use as a stand alone, or hand-held nerve monitoring apparatus, the present nerve monitoring system 10 and described artificially-induced mechanical muscle response detection algorithms (as described within method 100) may be used by a robotic surgical system, such as described in U.S. Pat. No. 8,855,622, issued Oct. 7, 2014 entitled "ROBOTIC SURGICAL SYSTEM WITH MECHANOMYOGRAPHY FEEDBACK," which is incorporated by reference in its entirety and for all of the disclosure set forth therein. In such a system, the above-described neural monitoring system 10 may be used to provide one or more control signals to a robotic surgical system if an artificially-induced mechanical muscle response is detected. In such an embodiment, the one or more elongate medical instruments 30 described above may be robotically controlled in up to 6 or more degrees of freedom/motion by a robotic controller. This instrument may be configured to perform a surgical procedure within an intracorporeal treatment area at the direction of the robotic controller, and may provide an electrical stimulus 38 in the manner described above. If an artificially-induced mechanical muscle response is detected, the neural monitoring system 10 may instruct the robotic controller (via the provided control signal) to limit the range of available motion of the elongate medical instrument 30 and/or to prevent an actuation of an end effector that may be disposed on the instrument 30 and controllable by the robotic controller.

While the best modes for carrying out the present technology have been described in detail, those familiar with the art to which this technology relates will recognize various alternative designs and embodiments that are within the scope of the appended claims. It is intended that all matter contained in the above description or shown in the accompanying drawings shall be interpreted as illustrative only and not as limiting.

Various advantages and features of the disclosure are further set forth in the following clauses:

Clause 1: A neural monitoring system for detecting an artificially-induced mechanical response of a muscle to a stimulus provided within an intracorporeal treatment area of a human subject, the intracorporeal treatment area including a nerve that innervates the muscle, the neural monitoring system comprising: a non-invasive mechanical sensor configured to be placed in mechanical communication with the muscle and to generate a mechanomyography output signal that corresponds to a sensed mechanical movement of the muscle; a stimulator configured to provide a periodic stimulus within the intracorporeal treatment area, the periodic stimulus including at least a first stimulus beginning at a first time (T1), and a second, consecutive stimulus beginning at a second time (T2); and a processor in communication with the mechanical sensor and the stimulator, the processor configured to: provide the periodic stimulus to the stimulator; receive the mechanomyography output signal from the mechanical sensor; analyze a response window of the mechanomyography output signal to determine if the first stimulus induced a response of the muscle; and provide an indication to a user if it is determined that the first stimulus induced a response of the muscle within the response window; wherein the response window corresponds to a period of time when an induced response to the first stimulus is likely to occur; and wherein the response window extends between a third time (T3) and a fourth time (T4) such that $T1 \leq T3 < T4 < T2$.

Clause 2: The neural monitoring system of clause 1, wherein the processor is further configured to determine if the first stimulus induced a response of the muscle by analyzing the mechanomyography output signal only within the response window.

Clause 3: The neural monitoring system of any of clauses 1-2, wherein the processor is configured to determine if the first stimulus induced a response of the muscle by examining one or more characteristics of the mechanomyography output signal within the response window using a supervised learning algorithm; and wherein the supervised learning algorithm is operative to classify the response window into one of a plurality of classifications comprising: the response window is representative of an artificially-induced mechanical response of the muscle; and the response window is not representative of an artificially-induced mechanical response of the muscle.

Clause 4: The neural monitoring system of clause 3, wherein the one or more characteristics of the mechanomyography output signal includes a graph of the amplitude of the mechanomyography output signal throughout the response window as a function of time; and wherein the supervised learning algorithm includes an image-based classifier operative to analyze one or more graphical aspects of the graph.

Clause 5: The neural monitoring system of any of clauses 1-4, wherein the mechanical sensor is a tri-axis accelerometer operative to monitor acceleration in three mutually orthogonal axes; and wherein the processor is configured to determine if the first stimulus induced a response of the muscle using a magnitude of a resultant vector calculated from the monitored acceleration in each of the three axes.

Clause 6: The neural monitoring system of clause 5, wherein the processor is configured to determine if the first stimulus induced a response of the muscle only if a magnitude of a movement of the muscle in a direction normal to the skin surface is greater than a magnitude of a movement of the muscle in a direction that is tangential to the skin surface.

Clause 7: The neural monitoring system of any of clauses 1-6, wherein $(T_4-T_3) \leq (T_2-T_1)/2$.

Clause 8: The neural monitoring system of any of clauses 1-7, wherein the processor is further configured to: identify signal content from the mechanomyography output signal that exists at least partially outside of the response window; determine a frequency component of the signal content; attenuate the frequency component from the mechanomyography output signal within the response window; and wherein the processor is configured to determine if the first stimulus induced a response of the muscle using the attenuated mechanomyography output signal within the response window.

Clause 9: The neural monitoring system of clause 8, wherein the signal content from the mechanomyography output signal exists at least partially between T1 and T2.

Clause 10: The neural monitoring system of any of clauses 8-9, wherein the periodic stimulus includes a plurality of stimuli; and wherein the signal content exists across the plurality of stimuli.

Clause 11: The neural monitoring system of any of clauses 1-10, wherein the processor is further configured to identify a time corresponding to a detected induced muscle response within the response window; determine a first response latency between the first stimulus and the time corresponding to a detected induced muscle response; identify a time corresponding to a subsequently detected muscle response that is induced by a subsequent stimulus provided by the stimulator; determine a second response latency between the subsequent stimulus and the time of the subsequently detected muscle response; provide an alert if the second response latency differs from the first response latency by more than a predetermined amount.

Clause 12: The neural monitoring system of any of clauses 1-11, wherein the first stimulus has a first current magnitude, a subsequent stimulus has a second current magnitude, and a detected induced muscle response to the first stimulus has a mechanomyography output signal magnitude; and wherein the second current magnitude is: different from the first current magnitude; and is a function of a difference between the mechanomyography output signal magnitude and a threshold output signal magnitude.

Clause 13: The neural monitoring system of clause 12, wherein the second current magnitude is proportional to the difference between the mechanomyography output signal magnitude and a threshold output signal magnitude.

Clause 14: A method of detecting an artificially-induced mechanical response of a muscle to a stimulus provided within an intracorporeal treatment area of a human subject, the intracorporeal treatment area including a nerve that innervates the muscle, the method comprising: transmitting a periodic electrical stimulus to a stimulator within the intracorporeal treatment area, the periodic stimulus including at least a first stimulus beginning at a first time (T1), and a second, consecutive stimulus beginning at a second time (T2); receiving a mechanomyography output signal from a non-invasive mechanical sensor in mechanical communication with the muscle, wherein the mechanomyography output signal corresponds to a sensed mechanical movement of the muscle; analyzing the mechanomyography output signal within a response window of time to determine if the sensed motion is representative of an artificially-induced response of the muscle, wherein the response window corresponds to a period when an induced response of the muscle to the first stimulus is likely to occur, the response window extending between a third time (T3) and a fourth time (T4) such that T1≤T3<T4<T2; and providing an indication to a user that the sensed motion is an artificially-induced muscle response only if the motion occurs within the response window.

Clause 15: The method of clause 14, further comprising: analyzing the mechanomyography output signal only within the response window to determine if the sensed motion is an artificially-induced muscle response.

Clause 16: The method of any of clauses 14-15, further comprising: examining one or more characteristics of the mechanomyography output signal within the response window using a supervised learning algorithm to determine if the sensed mechanical movement of the muscle is an artificially-induced muscle response; and wherein the supervised learning algorithm is operative to classify the mechanomyography output signal within the response window into one of a plurality of classifications comprising: the response window is representative of an artificially-induced mechanical response of the muscle; and the response window is not representative of an artificially-induced mechanical response of the muscle.

Clause 17: The method of any of clauses 14-16, wherein $(T_4-T_3) \leq (T_2-T_1)/2$.

Clause 18: The method of any of clauses 14-17, further comprising: identifying signal content from the mechanomyography output signal that exists at least partially outside of the response window; determining a frequency component of the signal content; attenuating the frequency component from the mechanomyography output signal within the response window; and determining the occurrence of a muscle event using the attenuated mechanomyography output signal within the response window.

Clause 19: The method of any of clauses 14-18, further comprising: identifying a time of the muscle response within the response window; determining a first response latency between T1 and the time of the muscle response; identifying a time of a second muscle response within a second response window following a third stimulus provided by the stimulator beginning at a third time (T3); determining a second response latency between T3 and the time of the second muscle response; providing an alert if the second response latency differs from the first response latency by more than a predetermined amount.

Clause 20: The method of any of clauses 14-19, wherein the first stimulus has a first current magnitude, the second stimulus has a second current magnitude, and the muscle response has a mechanomyography output signal magnitude; and wherein transmitting the periodic electrical stimulus includes transmitting the second current magnitude such that it is: different from the first current magnitude; and is a function of a difference between the mechanomyography output signal magnitude and a threshold output signal magnitude.

Clause 21: A mechanomyography sensor configured to be placed in mechanical communication with a muscle of a human subject, the mechanomyography sensor comprising: a non-invasive mechanical sensor operative to sense a mechanical movement of the muscle and to generate a mechanomyography output signal that corresponds to the sensed mechanical movement; a communication means for transmitting the mechanomyography output signal to a processor that is operative to: provide a periodic stimulus to a stimulator, including at least a first stimulus beginning at a first time (T1), and a second, consecutive stimulus beginning at a second time (T2); receive the mechanomyography output signal from the mechanical sensor; analyze the mechanomyography output signal within a response window to determine if the first stimulus induced a response of the muscle; wherein the response window corresponds to a period of time when an induced response to the first stimulus is likely to occur; and wherein the response window extends between a third time (T3) and a fourth time (T4) such that T1≤T3<T4<T2; and provide an indication to a user if it is determined that the first stimulus induced a response of the muscle within the response window.

Clause 22: The mechanomyography sensor of clause 21, wherein the mechanical sensor is a tri-axis accelerometer operative to monitor acceleration in three mutually orthogonal axes; and wherein the processor is further operative to determine if the first stimulus induced a response of the muscle using a magnitude of a resultant vector calculated from the monitored acceleration in each of the three axes.

Clause 23: The mechanomyography sensor of clause 22, wherein the processor is further operative to determine if the first stimulus induced a response of the muscle only if a magnitude of a movement of the muscle in a direction normal to the skin surface is greater than a magnitude of a movement of the muscle in a direction that is tangential to the skin surface.

The invention claimed is:

1. A neural monitoring system for detecting an artificially-induced mechanical response of a muscle to a stimulus provided within an intracorporeal treatment area of a human subject, the intracorporeal treatment area including a nerve that innervates the muscle, the neural monitoring system comprising:
a non-invasive mechanical sensor configured to be placed in mechanical communication with the muscle and to generate a mechanomyography output signal that corresponds to a sensed mechanical movement of the muscle;
a stimulator configured to provide a periodic stimulus within the intracorporeal treatment area, the periodic stimulus including at least a first stimulus beginning at a first time ($T_1$), and a second, consecutive stimulus beginning at a second time ($T_2$); and a processor in communication with the mechanical sensor and the stimulator, the processor configured to:
provide the periodic stimulus to the stimulator;
receive the mechanomyography output signal from the mechanical sensor;
analyze a response window of the mechanomyography output signal to determine if the first stimulus induced a response of the muscle; and
provide an indication to a user if it is determined that the first stimulus induced a response of the muscle within the response window;
wherein the response window corresponds to a period of time when an induced response to the first stimulus is likely to occur; and
wherein the response window extends between a third time ($T_3$) and a fourth time ($T_4$) such that $T_1 \leq T_3 < T_4 < T_2$.

2. The neural monitoring system of claim 1, wherein the processor is further configured to determine if the first stimulus induced a response of the muscle by analyzing the mechanomyography output signal only within the response window.

3. The neural monitoring system of claim 1, wherein the processor is configured to determine if the first stimulus induced a response of the muscle by examining one or more characteristics of the mechanomyography output signal within the response window using a supervised learning algorithm; and
wherein the supervised learning algorithm is operative to classify the response window into one of a plurality of classifications, the plurality of classifications comprising:
a first classification wherein the mechanomyography output signal within the response window is indicative of an artificially-induced mechanical response of the muscle; and
a second classification wherein the mechanomyography output signal within the response window is not indicative of an artificially-induced mechanical response of the muscle.

4. The neural monitoring system of claim 3, wherein the one or more characteristics of the mechanomyography output signal includes a graph of an amplitude of the mechanomyography output signal throughout the response window as a function of time; and
wherein the supervised learning algorithm includes an image-based classifier operative to analyze one or more graphical aspects of the graph.

5. The neural monitoring system of claim 1, wherein the mechanical sensor is a tri-axis accelerometer operative to monitor acceleration in three mutually orthogonal axes; and
wherein the processor is configured to determine if the first stimulus induced a response of the muscle using a magnitude of a resultant vector calculated from the monitored acceleration in each of the three axes.

6. The neural monitoring system of claim 5, wherein the processor is configured to determine if the first stimulus induced a response of the muscle only if a magnitude of a movement of the muscle in a direction normal to a skin surface is greater than a magnitude of a movement of the muscle in a direction that is tangential to the skin surface.

7. The neural monitoring system of claim 1, wherein $(T_4-T_3) \leq (T_2-T_1)/2$.

8. The neural monitoring system of claim 1, wherein the processor is further configured to:
identify signal content from the mechanomyography output signal that exists at least partially outside of the response window;
determine a frequency component of the signal content;
attenuate the frequency component from the mechanomyography output signal within the response window; and
wherein the processor is configured to determine if the first stimulus induced a response of the muscle using the attenuated mechanomyography output signal within the response window.

9. The neural monitoring system of claim 8, wherein the signal content from the mechanomyography output signal exists at least partially between $T_1$ and $T_2$.

10. The neural monitoring system of claim 8, wherein the periodic stimulus includes a plurality of stimuli; and
wherein the signal content exists across the plurality of stimuli.

11. The neural monitoring system of claim 1, wherein the processor is further configured to
identify a time corresponding to a detected induced muscle response within the response window;
determine a first response latency between the first stimulus and the time corresponding to a detected induced muscle response;
identify a time corresponding to a subsequently detected muscle response that is induced by a subsequent stimulus provided by the stimulator;
determine a second response latency between the subsequent stimulus and the time of the subsequently detected muscle response; and
provide an alert if the second response latency differs from the first response latency by more than a predetermined amount.

12. The neural monitoring system of claim 1, wherein the first stimulus has a first current magnitude, a subsequent stimulus has a second current magnitude, and a detected induced muscle response to the first stimulus has a mechanomyography output signal magnitude; and
wherein the second current magnitude is:
different from the first current magnitude; and
is a function of a difference between the mechanomyography output signal magnitude and a threshold output signal magnitude.

13. The neural monitoring system of claim 12, wherein the second current magnitude is proportional to the difference between the mechanomyography output signal magnitude and a threshold output signal magnitude.

14. A method of detecting an artificially-induced mechanical response of a muscle to a stimulus provided within an intracorporeal treatment area of a human subject, the intracorporeal treatment area including a nerve that innervates the muscle, the method comprising:
transmitting a periodic electrical stimulus to a stimulator within the intracorporeal treatment area, the periodic stimulus including at least a first stimulus beginning at a first time ($T_1$), and a second, consecutive stimulus beginning at a second time ($T_2$);
receiving a mechanomyography output signal from a non-invasive mechanical sensor in mechanical communication with the muscle, wherein the mechanomyography output signal corresponds to a sensed mechanical movement of the muscle;
analyzing the mechanomyography output signal within a response window of time to determine if the sensed motion is representative of an artificially-induced response of the muscle, wherein the response window corresponds to a period when an induced response of the muscle to the first stimulus is likely to occur, the response window extending between a third time ($T_3$) and a fourth time ($T_4$) such that $T_1 \leq T_3 < T_4 < T_2$; and providing an indication to a user that the sensed motion is an artificially-induced muscle response only if the motion occurs within the response window.

15. The method of claim 14, further comprising: analyzing the mechanomyography output signal only within the response window to determine if the sensed motion is an artificially-induced muscle response.

16. The method of claim 14, further comprising: examining one or more characteristics of the mechanomyography output signal within the response window using a supervised learning algorithm to determine if the sensed mechanical movement of the muscle is an artificially-induced muscle response; and
- wherein the supervised learning algorithm is operative to classify the mechanomyography output signal within the response window into one of a plurality of classifications, the plurality of classifications comprising:
  - a first classification wherein the mechanomyography output signal within the response window is indicative of an artificially-induced mechanical response of the muscle; and
  - a second classification wherein the mechanomyography output signal within the response window is not indicative of an artificially-induced mechanical response of the muscle.

17. The method of claim 14, wherein $(T_4-T_3) \leq (T_2-T_1)/2$.

18. The method of claim 14, further comprising:
identifying signal content from the mechanomyography output signal that exists at least partially outside of the response window;
determining a frequency component of the signal content;
attenuating the frequency component from the mechanomyography output signal within the response window; and
determining an occurrence of a muscle event using the attenuated mechanomyography output signal within the response window.

19. The method of claim 14, further comprising:
identifying a time of the muscle response within the response window;
determining a first response latency between $T_1$ and the time of the muscle response;
identifying a time of a second muscle response within a second response window following a third stimulus provided by the stimulator beginning at a third time ($T_3$);
determining a second response latency between $T_3$ and the time of the second muscle response; and
providing an alert if the second response latency differs from the first response latency by more than a predetermined amount.

20. The method of claim 14, wherein the first stimulus has a first current magnitude, the second stimulus has a second current magnitude, and the muscle response has a mechanomyography output signal magnitude; and
wherein transmitting the periodic electrical stimulus includes transmitting the second current magnitude such that the second current magnitude is:
different from the first current magnitude; and
is a function of a difference between the mechanomyography output signal magnitude and a threshold output signal magnitude.

* * * * *